United States Patent
Furze (10) Patent No.: US 6,757,353 B2
(45) Date of Patent: Jun. 29, 2004

(54) GOLF BALL INSPECTION USING METAL MARKERS

(75) Inventor: Paul A Furze, Tiverton, RI (US)

(73) Assignee: Acushnet Company, Fairhaven, MA (US)

(*) Notice: Subject to any disclaimer, the term of this patent is extended or adjusted under 35 U.S.C. 154(b) by 109 days.

(21) Appl. No.: 10/229,614

(22) Filed: Aug. 28, 2002

(65) Prior Publication Data

US 2004/0042586 A1 Mar. 4, 2004

(51) Int. Cl.⁷ .............................................. G01N 23/02
(52) U.S. Cl. ............................ 378/58; 378/62; 378/163
(58) Field of Search ............................. 378/62, 58, 162, 378/163

(56) References Cited

U.S. PATENT DOCUMENTS

| 6,160,870 A | 12/2000 | Jacobson | 378/165 |
| 6,312,346 B1 * | 11/2001 | Sugimoto | 473/370 |
| 6,390,937 B1 | 5/2002 | Marshall et al. | 473/374 |

\* cited by examiner

*Primary Examiner*—Craig E. Church
(74) *Attorney, Agent, or Firm*—William B. Lacy (57) ABSTRACT

A method for inspecting a golf ball comprising the steps of providing a golf ball comprising a core and a cover; providing at least one flat reference marker; abutting the golf ball against at least one marker; rotating the golf ball about a single axis; capturing an x-ray image of the golf ball and marker; and determining the eccentricity of the golf ball.

22 Claims, 6 Drawing Sheets

GOLF BALL INSPECTION USING METAL MARKERS

FIELD OF THE INVENTION

This invention relates generally to golf ball inspection. More particularly, this invention relates to golf ball inspection for concentricity of internal components using x-rays.

BACKGROUND OF THE INVENTION

While the majority of golf balls today are solid, back in the thirties, golf balls were generally only of wound construction. The wound ball was comprised of a center, windings, and a cover. One day, Philip E. Young decided to see if the wound golf ball center he was playing was concentric and asked his golfing partner, a dentist, to x-ray the ball. Sure enough, the x-ray showed that the center of his ball was not concentric. As a result, Mr. Young founded the Acushnet Process Company and began making golf balls that were all x-ray inspected for concentricity.

Heretofore, x-ray inspection of both solid and wound golf balls has been accomplished using two methods. The first method is the golden image process, which consists of taking an image of a "perfect" specimen (a control), placing it into memory, taking subsequent images of samples, and comparing them to the image of the "perfect" specimen. The differences between the "perfect" image and the specimen are used to determine the amount of error in the specimen.

The second method, typically for use on solid balls, includes the steps of x-raying the specimen in such a manner that both the core and the cover are displayed. X-raying the ball in this manner allows direct measurement of the thickness of the cover. This process generally requires the use of lower energy x-rays to so that the cover material can be seen clearly in the resulting image. Many times, the use of lower power causes the edges of the image to become distorted or less clear. The specimen can be doped to assist in cover detection.

Both methods may also include the step of doping the specimen so that the specimen is easier to x-ray. Doping a specimen, however, can have adverse effects on the product. The golden image process is additionally subject to error if the standard is at all less than perfect. Further, the positioning of the golf ball must be perfect. Any wobble in the fixture that holds the ball will affect the golden image test.

There are other limitations inherent in the micro focal x-ray machines that are utilized in industries such as the medical, integrated circuit, and printed circuit board industries. It should also be noted that simply using a micro focal x-ray is not sufficient to produce the sharp images required for many imaging techniques. The device for converting x-rays to visible light, called the image intensifier, must have sufficient resolution to produce a high quality image. Resolution is usually measured in line pairs per millimeter. For example, if an image intensifier has a resolution of 4 line pairs per millimeter and an optical gain of 2 it would be able to resolve an object ⅛ millimeter in size.

Because of these limitations and problems, there is, therefore, a need for more suitable methods of determining the concentricity and dimensions of golf ball components using x-rays. Such a method is presented by the present invention.

SUMMARY OF THE INVENTION

The present invention is directed to A method for inspecting a golf ball comprising the steps of providing a golf ball comprising a core and a cover; abutting the golf ball against at least one flat marker; rotating the golf ball about a single axis; capturing an x-ray image of the golf ball and at least one marker; and determining the eccentricity of the golf ball.

In one embodiment, the step of determining the eccentricity comprises the step of measuring the distance from the at least one marker to an outer surface of the core as the ball rotates about the single axis. The distance between the marker and the core surface are used to determine the cover thickness. Ideally, the marker is opaque to x-rays, such as with a metal marker. Preferably, the metal is aluminum, copper, steel, titanium, or a mixture thereof.

In another embodiment, there are at least two additional markers oriented to measure different axes. The x-ray has an intensity optimized for detecting the edge of the golf ball core. The core and the marker have a first and second center and the distance between the two is calculated at predetermined intervals to determine concentricity of the core. Ideally, the x-ray has a spot size of less than about 0.035 inches by 0.02 inches, preferably, less than about 0.01 inches by 0.01 inches, and most preferably, less than about 0.005 inches by 0.005 inches. It is preferred that the x-ray has an intensity greater than the intensity required to detect the cover material such that the cover is transparent. Additionally, the cover opacity and the core opacity should be different. In one preferred core construction, the core comprises a center and an outer core layer. The x-ray intensity is preferably between about 25 and about 75 kV, more preferably between about 30 and about 60 kV, and most preferably between about 35 and about 50 kV The present invention is also directed to a method for inspecting a golf ball comprising the steps of providing a golf ball comprising a core and a cover; restraining the golf ball between a flat surface and a rotating concave surface; rotating the golf ball about a single axis; providing at least two reference markers abutting the cover of the golf ball, wherein a first marker is embedded in and flush with the rotating concave surface and a second marker is on an axis perpendicular to the axis of rotation; capturing an x-ray image of the golf ball; measuring a first distance between the core center and the first marker and a second distance between the core center and the second marker; and determining the true eccentricity of the golf ball by combining the first and second distances using the following formula:

$$E_{True} = \sqrt{(E_1^2 + E_2^2)}$$

where $E_1$ is the eccentricity along the axis of rotation and $E_2$ is the eccentricity perpendicular to the axis. The flat surface and rotating concave surface can be aligned along the axis of rotation.

A method for inspecting a golf ball comprising the steps of providing a golf ball comprising a core and a cover; restraining the golf ball against a rotating fixture; rotating the golf ball about a single axis; providing at least two reference markers abutting the cover of the golf ball, wherein a first marker is embedded in the rotating fixture and abuts the cover, and a second marker is on an axis perpendicular to the axis of rotation; capturing an x-ray image of the golf ball; measuring a first distance between the core center and the first marker and a second distance between the core center and the second marker; and determining the true eccentricity of the golf ball by combining the first and second distances using the following formula:

$$E_{True} = \sqrt{(E_1^2 + E_2^2)}$$

where $E_1$ is the eccentricity along the axis of rotation and $E_2$ is the eccentricity perpendicular to the axis. The golf ball may be restrained against the rotating fixture with clamps.

DETAILED DESCRIPTION OF THE PREFERRED EMBODIMENTS

The present invention is directed to the use of metal markers to inspect and better locate the surface and concentricity of a golf ball using an electromagnetic energy source, such as x-rays. More particularly, the invention is directed to the x-ray inspection of golf balls incorporating markers opaque to x-ray imaging. The use of markers, and metal markers in particular, makes it easier to particularly locate the outer surface of the golf ball for comparison with inner surfaces, such as those defined by golf ball centers, cores, intermediate layers, and inner cover layers, when imaged with x-rays.

Metal markers are easily "seen" with x-ray imaging because of their lack of transmission of x-ray energy. X-rays are high-energy photons that have higher energy and a shorter wavelength (typically about 0.3 nm to about 2 nm), compared to the energy and wavelength (about 400 nm to about 780 nm) of visible light. Anytime there is more matter between the x-ray source and the detection film, whether the matter is thicker or just has a higher density, fewer x-rays are transmitted to the detection film, which starts off whitish and darkens as various levels of x-rays strike it. For example, bones appear lighter on a typical human x-ray image because bone is denser than the rest of the body, and in dental x-rays, metal fillings appear white, because the metal is very dense.

Figure 5:
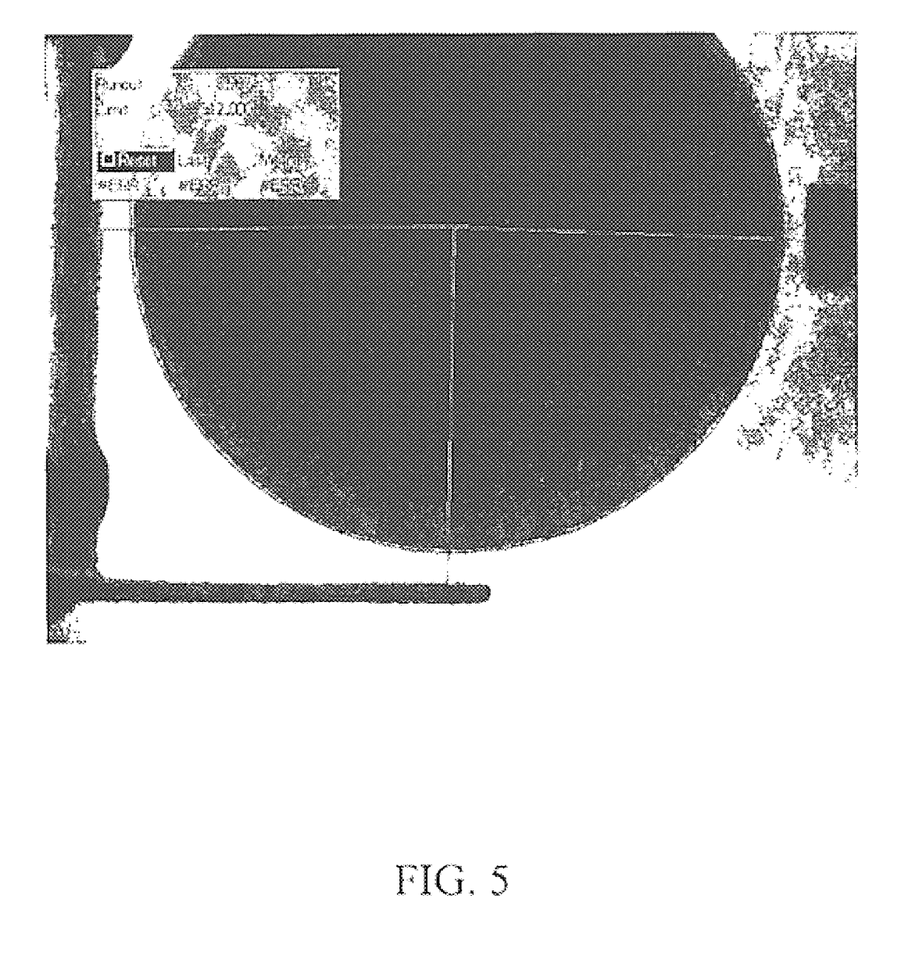
FIG. 5 is an x-ray image at an intensity set to detect both cover and core.
Figure 6:
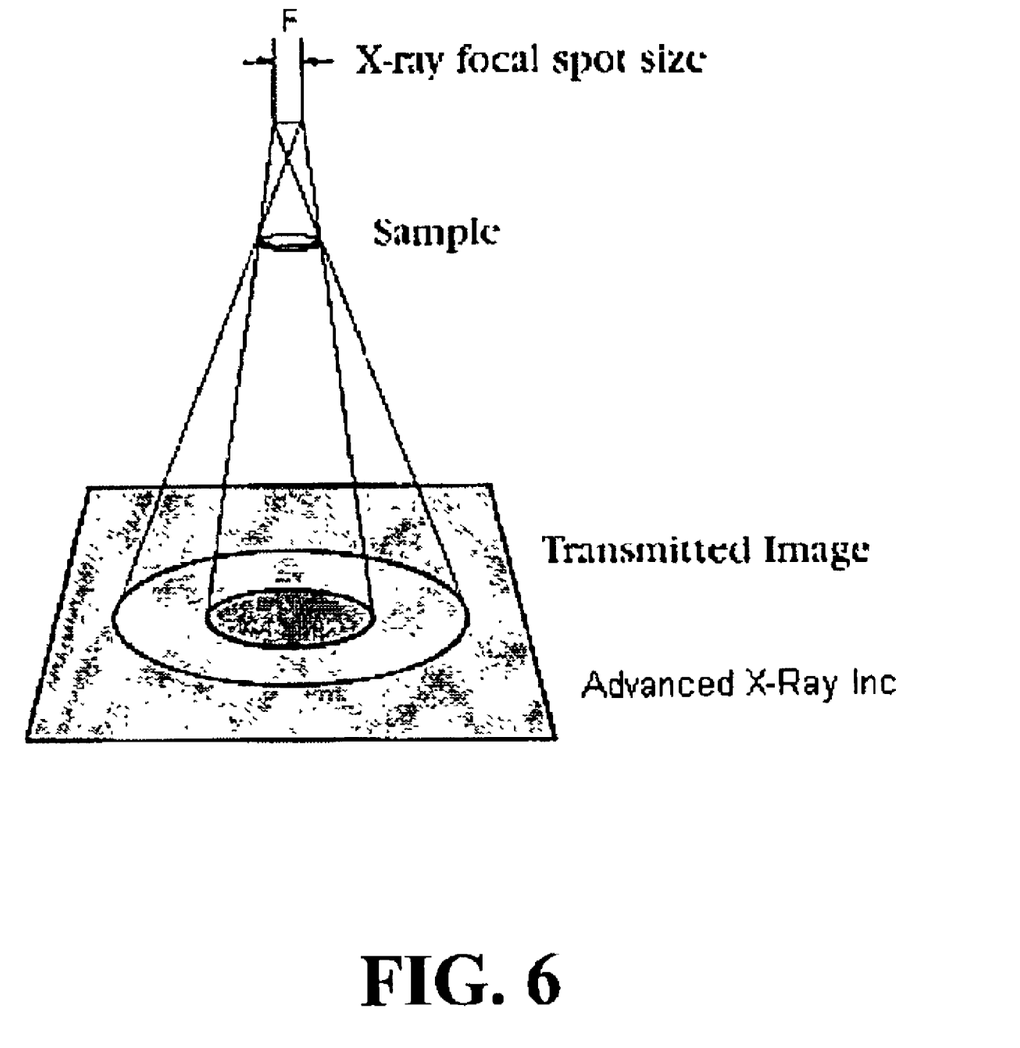
FIG. 6 is an x-ray image at an intensity set to detect only the core.

The marker(s) of the present invention are opaque to x-rays and, therefore, provide a very clear and defined edge and reference point from which to measure core and layer dimensions against. Because the optimal x-ray intensity for clearly discerning the core and its edges is much higher than the x-ray intensity that allows clear edge definition of the cover, the metal markers allow the x-ray intensity to be optimized for detecting the edge of the golf ball core without being concerned with seeing and using the cover as a reference point. Without the markers, the x-ray intensity must be set at a compromising intensity where both cover and core can be seen (but with reduced contrast and definition). Referring to FIG. 5, the x-ray image of the golf ball was taken at an intensity set to detect both the cover and the core. At this intensity, the surface of the cover appears irregular and, the surface of the core is out of focus. In FIG. 6, the x-ray intensity is set much higher, optimized for core detection. FIG. 6 clearly shows that, at the higher x-ray intensity, the surface of the cover is undetectable without the presence of the metal marker.

Preferably, one or more metal marker(s) are used, more preferably greater than about two, and most preferably, at least about three. The metal markers can be constructed of any material opaque to x-rays, but are preferably metal or blend of metals. More preferably, the markers are aluminum, steel, copper, or titanium. If more than one markers are present, they can to be of the same or differing materials or metals.

In a preferred embodiment, the golf ball can be rotated and the center of the ball calculated from the curved edge measurement. Then the distance from the center to the metal marker can be calculated at predetermined intervals to determine concentricity of the core.

In another preferred embodiment, the ball can be simultaneously measured on multiple axes. This improves the measurement of concentricity by making it possible to detect whether the core is shifted, no matter which direction it is shifted.

Figure 1:
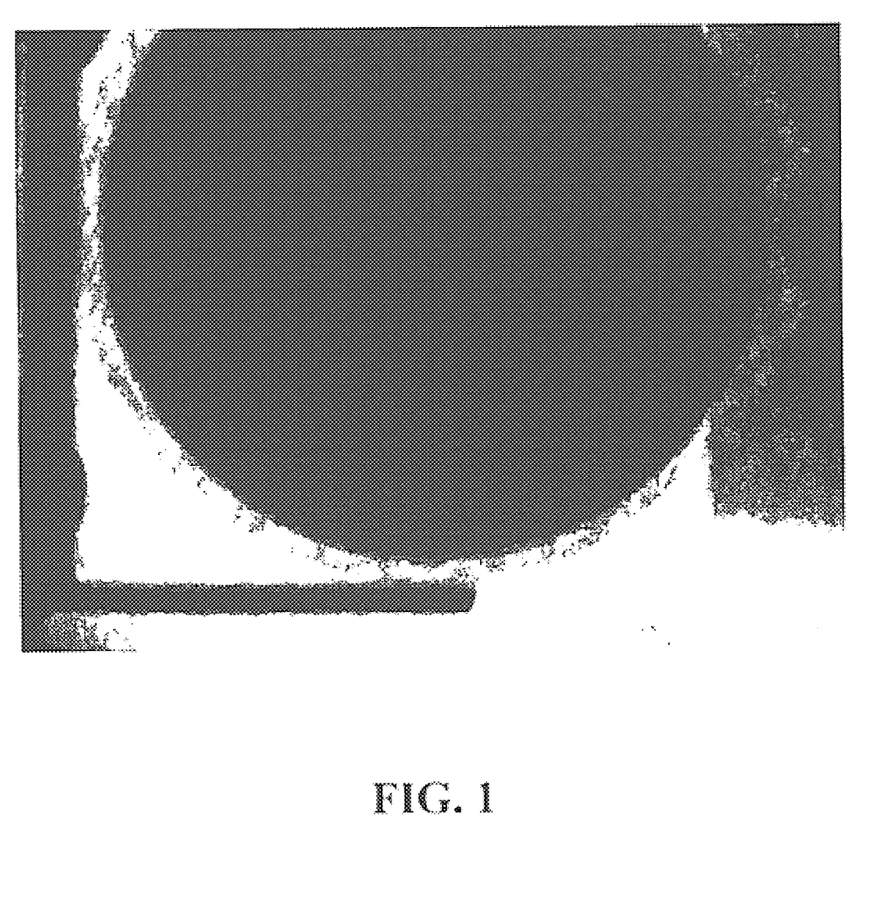
FIG. 1 is a cross-sectional view of a golf ball shifted along an axis of rotation.
Figure 2:
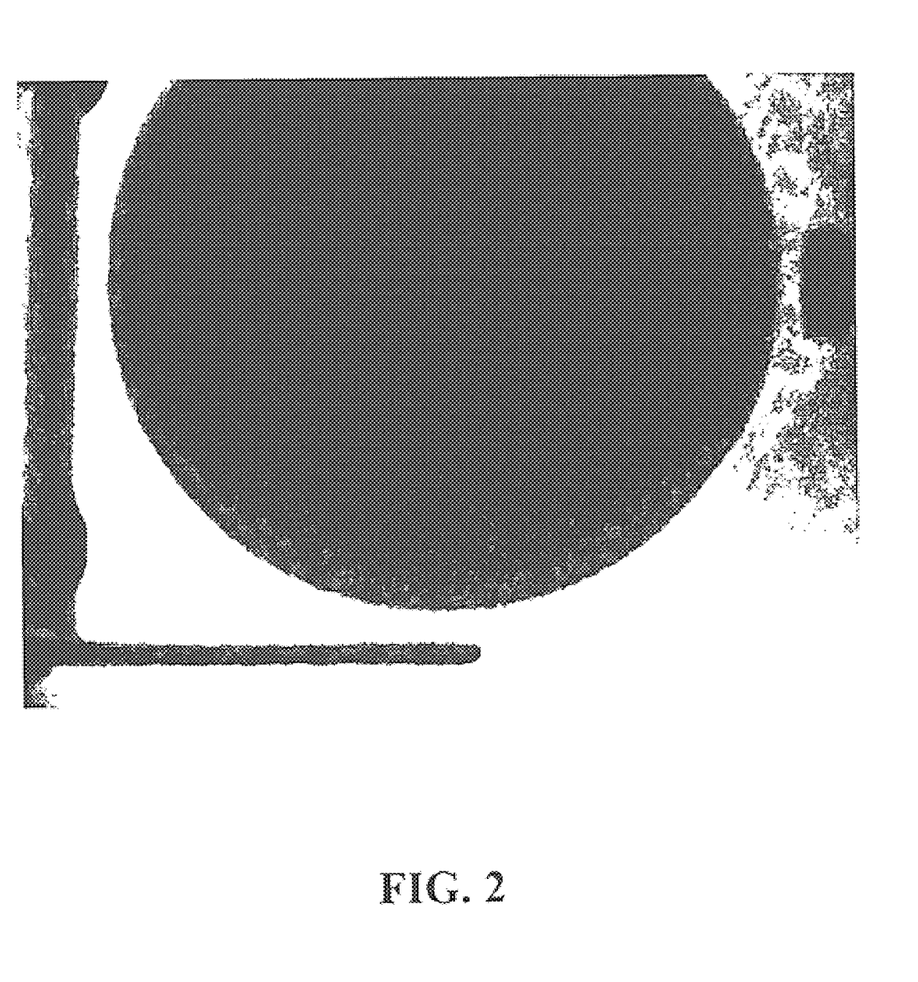
FIG. 2 is a cross-sectional view of a golf ball and possible eccentricity errors.

Referring to FIGS. 1 and 2, when a ball is rotated about an axis to measure the eccentricity of its core, what is typically done is that the distance from the surface to the core is measured repeatedly as it rotates. The difference between the maximum distance and the minimum distance is measured and indicates how far off center the core is. However, the only eccentricity that is detected is that which is perpendicular to the axis of rotation. If the core happens to be shifted along the axis of rotation no eccentricity is detected at all. If the core is shifted at some angle to the axis of rotation, the measured eccentricity is less than the true eccentricity by the sine of the angle. According to the present invention, in order to find the true eccentricity of the core, it is necessary to measure along the axis of rotation as well as perpendicular to it.

Figure 4:
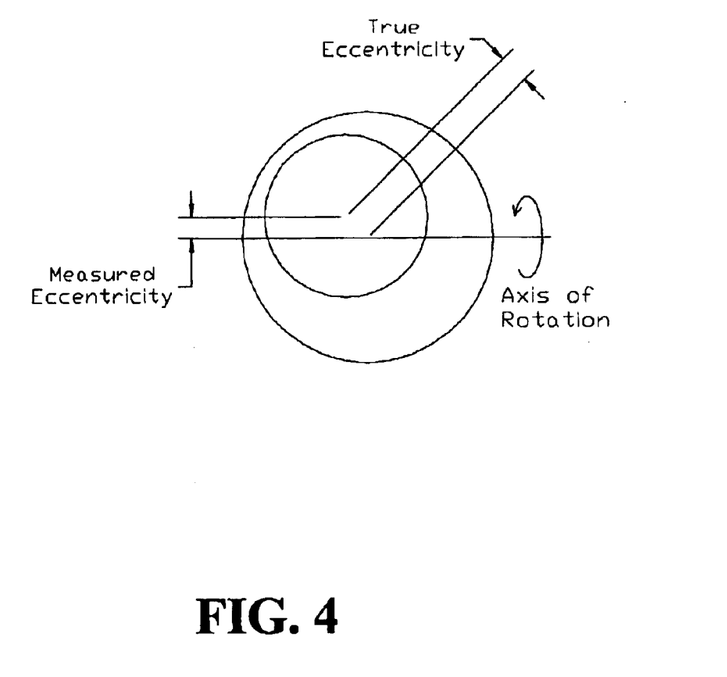
FIG. 4 is a golf ball x-ray image according to the present invention.

Referring to FIG. 4, the x-ray image of a golf ball shows it being rotated along its horizontal axis. In a preferred embodiment, the ball is rotated about an axis and the distance from the surface to the center of the core is measure repeatedly. The intersecting lines indicate measurements from the center of the core to the metal markers. The difference between the maximum and minimum distance measure is taken to determine how far off center the core is. The measurements are taken along the axis of rotation as well as perpendicular to the axis. Thus, there are at least two measurements of eccentricity and they are preferably combined using the Pythagorean theorem.

$$E_{True} = \sqrt{(E_1^2 + E_2^2)}$$

The true eccentricity ($E_{True}$) is the square root of the eccentricity along the axis of rotation ($E_1$), squared, plus the eccentricity perpendicular to the axis ($E_2$), squared.

Figure 3:
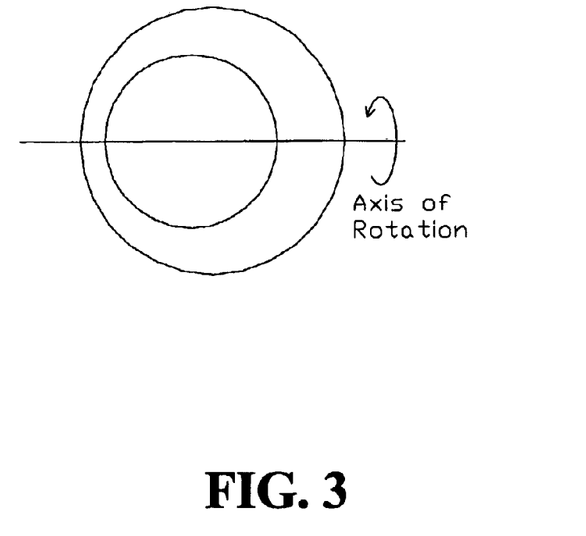
FIG. 3 is a depiction of x-ray focusing optics and the resulting spot size and error.

Referring to FIG. 3, because of the nature of the preferred x-ray source (transmission type) and the lack of focusing lenses, the quality of the image and the ability to resolve fine details is dependent on the size of the spot the radiation emanates from (the focal spot). Preferably, the x-ray source used has a small x-ray focal spot size. In general, x-ray spot size is around 0.035 inches by 0.02 inches. The resulting "band of unsharpness," seen in FIG. 3, is about 0.017 inches to about 0.010 inches. While this unsharpness is not a problem for imaging many types of golf balls, it can be a problem for golf balls having cover layers of less than about 0.05 inches. In a preferred embodiment, therefore, the x-ray focal spot size in the present invention is less than about 0.01 inches by 0.01 inches. In a more preferred embodiment, the x-ray focal spot size is less than about 0.005 inches by 0.005 inches. It is envisioned that a single lens or a combination of lenses may be used to adjust the x-ray spot size to a desired area.

Figure 7:
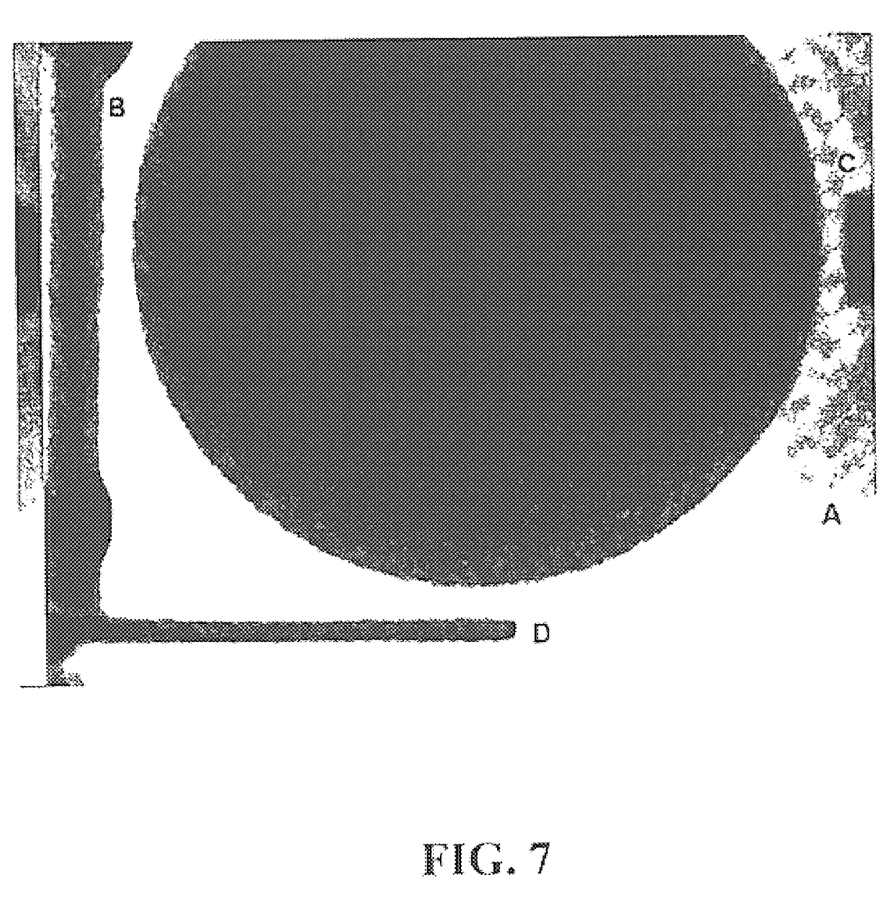
FIG. 7 is an x-ray image depicting the markers and golf ball imaging system of the present invention.

Referring to FIG. 7, preferably a golf ball is clamped between a rotating cup A and a flat surface B. The cup A is made of a plastic material, intended to be relatively transparent to x-rays. Inside the cup A, a metal marker C is held against the golf ball by a spring. The flat surface B is also made of a plastic material with a 0.06-inch covering of aluminum that serves as the metal marker C. A piece of spring steel D that contacts the ball on its equator as it rotates constitutes another metal marker.

The image analysis is accomplished using an Insight® 2000 by Cognex, of Natick, Mass. In a first method, the edge of the core and the edge of the marker are determined using the "find edge" tool and the distance between the core and the marker are measured at multiple locations around the ball to calculate eccentricity. In a preferred method the core of the golf ball is located with a "find curve" tool. Each of the metal markers is located by finding their edges, the edge adjacent the ball and the opposing edge, with a "find edge" tool. From this step, the middle of the marker is determined by obtaining the difference between the two edges. From this determination, the center of the golf ball core to the center, of each of the markers can be determined. In a most preferred method, the core of the golf ball is located with a "find curve" tool. The center of each of the metal markers is located using the,"find pattern" tool. The "find curve" and "find pattern" tools gave the most accurate and repeatable measurements.

The center of the core and center of the markers are determined because changes to the x-ray intensity can alter the apparent size of an object, but do not effect the actual location. As the x-ray intensity is increased, for example, the core may appear to decrease in diameter while the center remains in the same location. It is believed that this effect results from the large focal spot size of the x-ray source (roughly 0.9 mm×0.5 mm), as described above in depicted in FIG. 3.

Below is a table that compares the results of x-ray and another common method of obtaining golf ball dimensions, ultrasonic measurements. The ultrasonic measurements are of a urethane outer cover and mantle layer measured at 90° intervals all around the ball. The eccentricity was calculated using the square root of the sum of the squares, as described above. The identical golf balls were x-ray inspected a variety of times using the method of the invention. X-ray eccentricity is expressed as a range from the highest to the lowest value obtained.

TABLE 1

| Ball # | Ultrasonic Measurements | | | | | | | X-ray |
| --- | --- | --- | --- | --- | --- | --- | --- | --- |
| | Bottom | Left | Right | Front | Back | Top | Eccentricity | Eccentricity |
| Good #4 | 38 | 34 | 40 | 39 | 36 | 38 | 3.35 U.S.C. § | 2.1–10.5 |
| Good #2 | 41 | 40 | 41 | 42 | 39 | 34 | 3.84 | 3.0–7.3 |
| Good #9 | 38 | 39 | 36 | 42 | 36 | 34 | 3.91 | 3.8–11.5 |
| Good #6 | 35 | 35 | 34 | 36 | 34 | 40 | 2.74 | 2.8–7.9 |
| Good #12 | 34 | 32 | 35 | 35 | 33 | 40 | 3.50 | 4.6–8.4 |
| Bad #6 | 37 | 38 | 36 | 35 | 36 | 23 | 7.09 | 13.8–18.5 |
| Bad #4 | 36 | 43 | 37 | 37 | 37 | 24 | 6.71 | 15–20.7 |
| Bad #5 | 36 | 37 | 37 | 34 | 34 | 26 | 5.00 | 12.6–17.3 |
| Bad #12 | 36 | 36 | 37 | 36 | 38 | 25 | 5.61 | 11.8–17 |

The term "about," as used herein in connection with one or more numbers or numerical ranges, should be understood to refer to all such numbers, including all numbers in a range.

The invention described and claimed herein is not to be limited in scope by the specific embodiments herein disclosed, since these embodiments are intended solely as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A method for inspecting a golf ball comprising the steps of:
   providing a golf ball comprising a core and a cover;
   abutting the golf ball against at least one flat marker;
   rotating the golf ball about a single axis;
   capturing an x-ray image of the golf ball and at least one marker; and
   determining the eccentricity of the golf ball.

2. The method of claim 1, wherein the step of determining the eccentricity comprises the step of measuring the distance from the at least one marker to an outer surface of the core as the ball rotates about the single axis.

3. The method of claim 2, wherein the distance between the marker and the core surface are used to determine the cover thickness.

4. The method of claim 1, wherein the marker is opaque to x-rays.

5. The method of claim 1, wherein the marker is metal.

6. The method of claim 5, wherein the metal is aluminum, copper, steel, titanium, or a mixture thereof.

7. The method of claim 1, further comprising at least two markers oriented to measure different axes.

8. The method of claim 1, where the x-ray has an intensity optimized for detecting the edge of the golf ball core.

9. The method of claim 1, wherein the x-ray intensity is between about 25 and about 75 kV.

10. The method of claim 9, wherein the x-ray intensity is between about 30 and about 60 kV.

11. The method of claim 10, wherein the x-ray intensity is between about 35 and about 50 kV.

12. The method of claim 1, where the core and the marker have a first and second center and the distance between the two is calculated at predetermined intervals to determine concentricity of the core.

13. The method of claim 1, wherein the x-ray has a spot size of less than about 0.035 inches by 0.02 inches.

14. The method of claim 13, wherein the x-ray has a spot size of less than about 0.01 inches by 0.01 inches.

15. The method of claim 14, wherein the x-ray has a spot size of less than about 0.005 inches by 0.005 inches.

16. The method of claim 1, wherein the x-ray has an intensity greater than the intensity required to detect the cover material such that the cover is transparent.

17. The method of claim 1, wherein the cover has a first opacity and the core has a second opacity different from the first.

18. The method of claim 1, wherein the core comprises a center and an outer core layer.

19. A method for inspecting a golf ball comprising the steps of:
   providing a golf ball comprising a core and a cover;
   restraining the golf ball between a flat surface and a rotating concave surface;
   rotating the golf ball about a single axis;
   providing at least two reference markers abutting the cover of the golf ball, wherein a first marker is embedded in and flush with the rotating concave surface and a second marker is on an axis perpendicular to the axis of rotation;
   capturing an x-ray image of the golf ball;
   measuring a first distance between the core center and the first marker and a second distance between the core center and the second marker; and
   determining the true eccentricity of the golf ball by combining the first and second distances using the following formula:

$$E_{True} = \sqrt{(E_1^2 + E_2^2)}$$

where $E_1$ is the eccentricity along the axis of rotation and $E_2$ is the eccentricity perpendicular to the axis.

20. The method of claim 19, wherein the flat surface and rotating concave surface are aligned along the axis of rotation.

21. A method for inspecting a golf ball comprising the steps of:
   providing a golf ball comprising a core and a cover;
   restraining the golf ball against a rotating fixture;
   rotating the golf ball about a single axis;
   providing at least two reference markers abutting the cover of the golf ball, wherein a first marker is embedded in the rotating fixture and abuts the cover, and a second marker is on an axis perpendicular to the axis of rotation;
   capturing an x-ray image of the golf ball;
   measuring a first distance between the core center and the first marker and a second distance between the core center and the second marker; and
   determining the true eccentricity of the golf ball by combining the first and second distances using the following formula:

$$E_{True} = \sqrt{(E_1^2 + E_2^2)}$$

where $E_1$ is the eccentricity along the axis of rotation and $E_2$ is the eccentricity perpendicular to the axis.

22. The method of claim 21, wherein the golf ball is restrained against the rotating fixture with clamps.

* * * * *